（12） United States Patent
Thomas et al.

(10) Patent No.: US 7,560,566 B2
(45) Date of Patent: Jul. 14, 2009

(54) PROCESS FOR PRODUCING HETEROAROMATIC CARBOXYLIC ACIDS

(75) Inventors: William Barry Thomas, Middlesbrough (GB); Keith Whiston, Darlington (GB); Eduardo Cepeda Garcia-Verdugo, Nottingham (GB); Martyn Poliakoff, Nottingham (GB); Paul Anthony Hamley, Nottingham (GB)

(73) Assignee: INVISTA North America S.a.r.l., Wilmington, DE (US)

( * ) Notice: Subject to any disclaimer, the term of this patent is extended or adjusted under 35 U.S.C. 154(b) by 525 days.

(21) Appl. No.: 10/954,598

(22) Filed: Oct. 1, 2004

(65) Prior Publication Data

US 2007/0232807 A1 Oct. 4, 2007

(51) Int. Cl.
*C07D 213/80* (2006.01)
*C07D 239/00* (2006.01)

(52) U.S. Cl. ........................ 546/320; 544/242
(58) Field of Classification Search .................. 564/93, 564/320; 546/93, 320; 544/242
See application file for complete search history.

(56) References Cited

U.S. PATENT DOCUMENTS 2,245,528 A * 6/1941 Loder ..................... 562/417

3,354,202 A 11/1967 Zimmerschied et al.
5,171,880 A * 12/1992 Masilamani et al. ........ 562/411
6,765,113 B2 * 7/2004 Graham et al. ............. 562/413

FOREIGN PATENT DOCUMENTS

| DE | 19822788 | 10/1988 |
| JP | 07233150 | 9/1995 |
| JP | 2002-226404 | 8/2002 |
| WO | WO 02/06201 | 1/2002 |

OTHER PUBLICATIONS

Lin, Smith et al., International Journal of Chemical Kinetics, vol. 23, 1991, p. 971.
Holiday, R.L., J. Supercritical Fluids 12, 1998, p. 255-260.

* cited by examiner

*Primary Examiner*—Taylor Victor Oh
(74) *Attorney, Agent, or Firm*—Craig M. Sterner

(57) ABSTRACT

A process for the production of a heteroaromatic carboxylic acid comprising contacting in the presence of a catalyst, a precursor of said carboxylic acid with an oxidant, such contact being effected with said precursor and the oxidant in an aqueous solvent comprising water under supercritical conditions or near supercritical conditions close to the supercritical point.

8 Claims, 6 Drawing Sheets

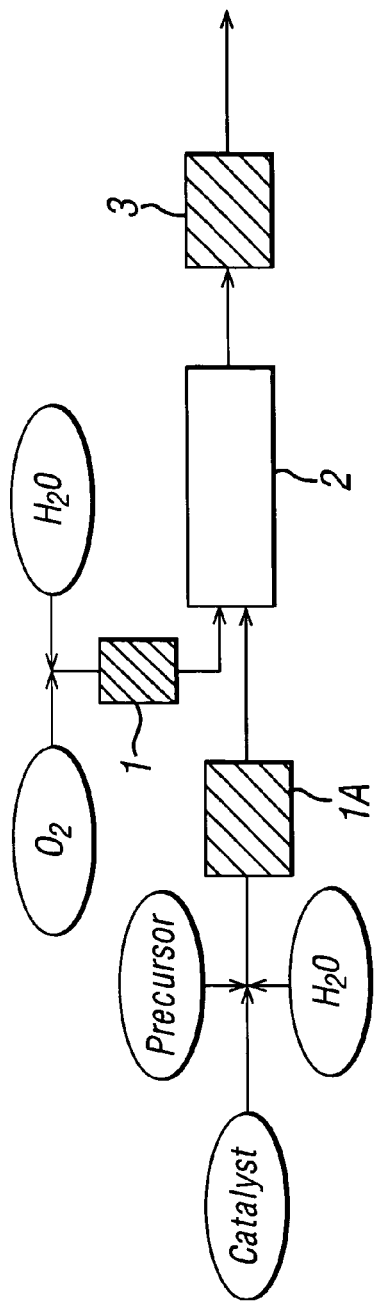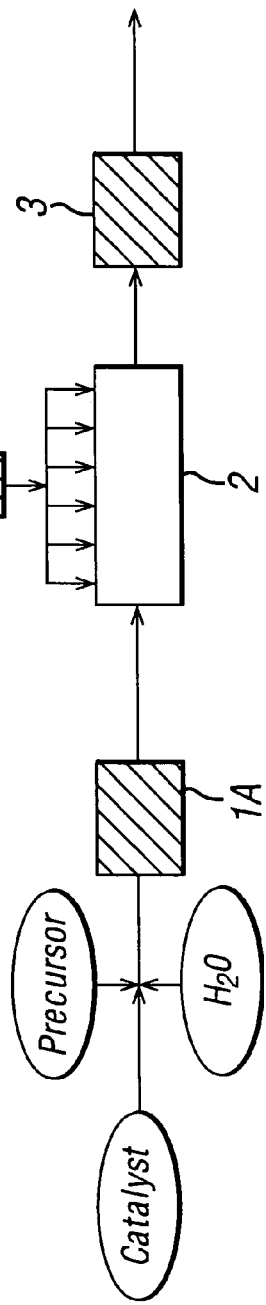

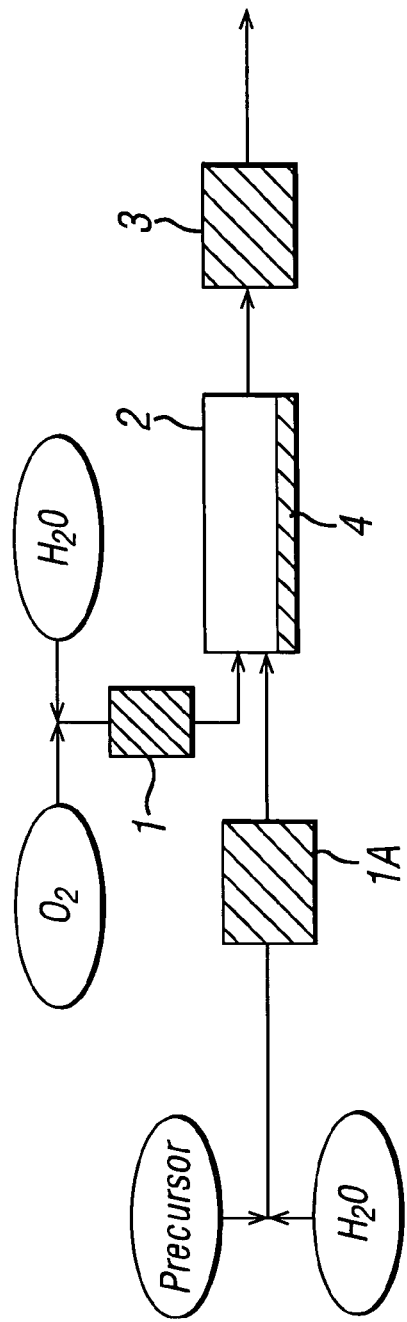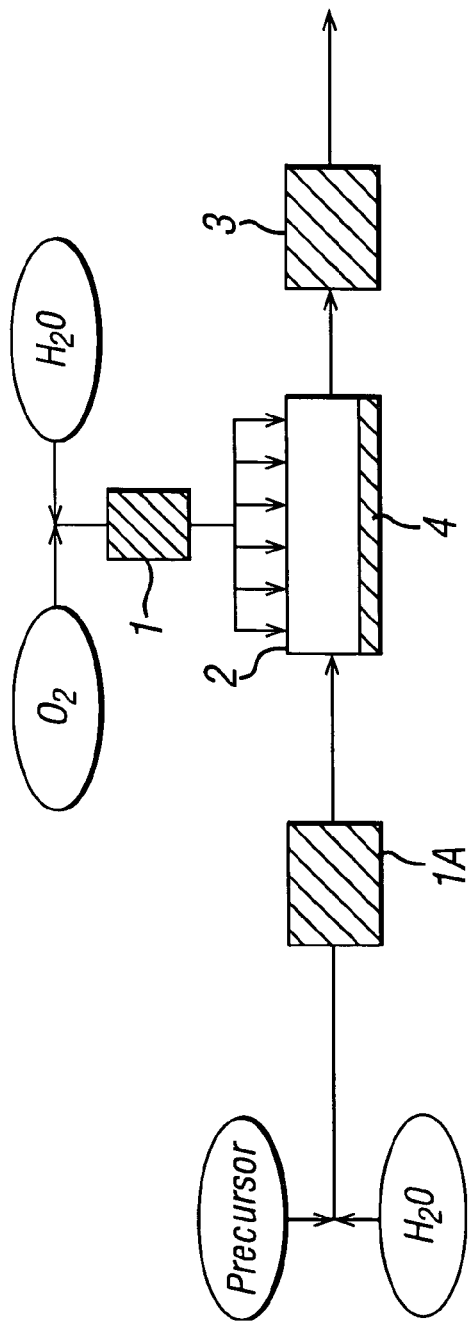

PROCESS FOR PRODUCING HETEROAROMATIC CARBOXYLIC ACIDS

BACKGROUND OF THE INVENTION

This invention relates to a process for the selective partial oxidation of alkylheteroaromatic compounds, particularly nitrogen-containing heteroaromatics, for the production of heteroaromatic carboxylic acids, such as nicotinic acid.

Pyridinecarboxylic acids derived from methylpyridines are important intermediates in the pharmaceutical industry. In particular, 3-pyridinecarboxylic acid or nicotinic acid, which is used as a precursor of vitamin B3, has been manufactured on a large scale. Two basic methods are employed for the synthesis of pyridinecarboxylic acids. One method is based on the hydrolysis of pyridinecarboxamides derived from pyridinecarbonitriles, and the other is the oxidation of alkylpyridines by air, nitric acid, selenium dioxide etc. The ammoxidation of methylpyridines forms pyridinecarbonitriles, which are subsequently hydrolyzed to pyridinecarboxylic acids through pyridinecarboxamides. 3-Pyridinecarboxylic acid has been commercially manufactured by nitric acid oxidation of 5-ethyl-2-methylpyridine.

The selective oxidation of alkyl heteroaromatic compounds to the carboxylic acid is known to be significantly more difficult than the corresponding carbocyclic compounds. The residence time required for the oxidation of alkyl heteroaromatic compounds to the carboxylic acid is significantly higher than for the equivalent carbocyclic alkyl aromatic compounds. For example, JP-07233150 (Nissan Chemical International) disclosed a process for the production of nicotinic acid from 3-methyl pyridine by oxidation in acetic acid using a Cobalt Manganese Cerium Bromide catalyst for which the required reaction time was 3 hours. Similar studies for p-xylene to terephthalic acid oxidation give a required residence time of 40 minutes or less (U.S. Pat. No. 3,354,202).

Conventional methods require long residence times, and produce significant amounts of undesirable by-products. By-products include partially-oxidised intermediates of the target carboxylic acid, such as aldehyde intermediates. For instance, the oxidation of 3-methylpyridine (3-Mpy) to produce 3-pyridinecarboxylic acid (3-PyA), can result in significant levels of 3-pyridinecarboxaldehyde (3-PyAl). In addition, decarboxylation of the product can give rise to the unsubstituted heteroaromatic compound itself, which is pyridine in the oxidation of 3-methylpyridine.

JP-2002-226404 (Daicel Chemical Industries Ltd) disclosed a process for the production of nicotinic acid from 3-methyl pyridine in acetic acid using N-hydroxyphthalimide as a promoter for oxidation in acetic acid. However, the process requires long residence times and is economically unfeasible since it produces substantial quantities of phthalimide and phthalate impurities from the added promoter.

The commercial gas phase process for the oxidation of 3-methylpyridine to nicotinic acid described in DE-19822788 (Lonza AG) suffers from several disadvantages. Since the reaction is exothermic, carrying it out in the gas phase gives rise to heat transfer limitations that reduce the efficiency with which energy can be removed from the reaction. Also since the reaction is carried out over a fixed bed heterogeneous catalyst, reaction can only occur at the surface of the catalyst rather than throughout the fluid medium.

There remains a need to provide improved processes for the production of heteroaromatic carboxylic acids, particularly one in which reaction times and by-product formation are reduced.

It would also be desirable to avoid the use of substantial amounts of organic solvent, such as acetic acid, which is relatively costly and, due to environmental restrictions, may require recovery and recycling. A further problem with the use of acetic acid is that it is flammable when mixed with air or oxygen under certain conditions. A further problem with the use of organic solvents is that the oxidant may have low solubility therein. For instance, where dioxygen is used as the oxidant, the dioxygen is present predominantly as discrete bubbles in the reaction medium with only a small proportion of the dioxygen dissolving in the solvent. To the extent that the reaction between the precursor and the dioxygen results from the dioxygen diffusing from the bubbles into the bulk liquid, the reaction rate is limited by the low solubility of dioxygen in the solvent.

It has now been found that heteroaromatic carboxylic acids can be synthesised by oxidation of a precursor in supercritical water.

Holliday R. L. et al (J. Supercritical Fluids 12, 1998, 255-260) describe a batch process for the synthesis of, inter alia, aromatic carboxylic acids from alkyl aromatics in a reaction medium of sub-critical water using molecular oxygen as the oxidant. The dielectric constant of water decreases dramatically from a room temperature value of around 80 $C^2/Nm^2$ to a value of 5 $C^2/Nm^2$ as it approaches its critical point (374° C. and 220.9 bara), allowing it to solubilise organic molecules. As a consequence, water then behaves like an organic solvent to the extent that hydrocarbons, e.g. toluene, are completely miscible with the water under supercritical conditions or near supercritical conditions. Terephthalic acid, for instance, is virtually insoluble in water below about 200° C. Dioxygen is also highly soluble in sub- and super-critical water.

International patent application WO 02/06201 discloses a continuous process for the production of aromatic carboxylic acids, such as terephthalic acid or isophthalic acid, comprising oxidising one or more precursors of the carboxylic acid in an aqueous solvent under supercritical conditions or near supercritical conditions close to the supercritical point.

It is an object of this invention to provide an alternative and improved process for the production of a heteroaromatic carboxylic acid in high yield and selectivity, and with reduced reaction times, and wherein the need to use an organic material as solvent is eliminated. It is a further object of this invention to provide an alternative and improved process for the production of a heteroaromatic carboxylic acid wherein substantially all the reactants and product are maintained in a common phase during reaction.

SUMMARY OF THE INVENTION

According to the present invention, there is provided a process for the production of a heteroaromatic carboxylic acid comprising contacting in the presence of a catalyst, a precursor of said carboxylic acid with an oxidant, such contact being effected with said precursor and the oxidant in an aqueous solvent comprising water under supercritical conditions or near supercritical conditions close to the supercritical point.

The process of the present invention is advantageous in that it involves short residence times and exhibits high yield and good selectivity of product formation. In addition, by employing water under supercritical or near supercritical conditions, the desired heteroaromatic carboxylic acid can be produced without employing aliphatic carboxylic acids such as acetic acid as the primary solvent.

Substantially all the carboxylic acid produced is maintained in solution during the reaction, and thereafter the carboxylic acid is recovered from the reaction medium.

Preferably, the process is carried out with the reactants and the solvent forming a substantially single homogeneous fluid phase in which the components in question are mixed at a molecular level. This is in contrast with existing processes where the dioxygen is present as discrete bubbles in the reaction medium. To the extent that the reaction between the precursor and dioxygen results from dioxygen diffusing from the bubbles into the bulk liquid, the reaction rate of a conventional process is limited by the solubility of dioxygen in the organic solvent, which is not high. The use of water under supercritical or near supercritical conditions as the solvent transforms the reaction kinetics since the concentration of dioxygen in water increases markedly as the supercritical point is approached and exceeded. Moreover, the reaction kinetics are further enhanced by the high temperatures prevailing when the water solvent is under supercritical or near supercritical conditions. The combination of high temperature, high concentration and homogeneity mean that the reaction to convert the precursor to the carboxylic acid can take place extremely rapidly compared with the residence times employed in a conventional process.

Under these conditions, an intermediate impurity, such as an aldehyde intermediate, is readily oxidised to the desired carboxylic acid. In addition, autocatalytic destructive reaction between the precursor and the oxidant and of consumption of catalyst is minimised.

Preferably, said contact is effected such that the precursor, oxidant and aqueous solvent constitute a substantially single homogeneous phase in the reaction zone, wherein the contact of at least part of said precursor with said oxidant is contemporaneous with contact of said catalyst with at least part of said oxidant.

Preferably, said contact is effected within a continuous flow reactor. In an alternative embodiment, the process may be conducted as a batch reaction in a batch-type reactor.

The process may be used to prepare heteroaromatic carboxylic acids containing 1, 2 or 3 heteroatoms, preferably 1 or 2 heteroatoms, and more preferably 1 heteroatom, preferably selected from nitrogen and oxygen, preferably nitrogen. Preferably the heteroaromatic carboxylic acids comprise 5 or 6-membered ring systems, preferably 6-membered ring systems. Preferably the heteroaromatic carboxylic acids are mono- or bi-cyclic, preferably mono-cyclic. The process is particularly applicable to the production of nitrogen-containing heteroaromatic compounds, particularly those comprising 1, 2 or 3 nitrogen atoms, and particularly those comprising a 6-membered ring. In a preferred embodiment, the heteroaromatic carboxylic acid comprises a pyridine or pyrimidine ring, preferably a pyridine ring. In a preferred embodiment, the heteroaromatic carboxylic acid is nicotinic acid.

Suitable precursors are alkyl-substituted heteroaromatic compounds, particularly methyl-substituted heteroaromatic compounds. In a preferred embodiment, the precursor is an alkylpyridine or alkylpyrimidine, preferably an alkylpyridine, preferably a methylpyridine, preferably 3-methylpyridine. In the processes described herein, preferably only one precursor of the desired carboxylic acid is used. Alternatively, however, more than one precursor of the desired carboxylic acid may be used. Besides alkyl substituents, the heterocyclic precursor may optionally have one or more other substituents, for example hydroxy, nitrate and halide group(s).

DETAILED DESCRIPTION OF THE INVENTION

In the process of the invention, the pressure and temperature of the process are selected to secure supercritical or near supercritical conditions. Thus, operating temperatures are typically in the range of 300 to 480° C., more preferably 330 to 450° C., typically from a lower limit of about 340 to 370° C. to an upper limit of about 370 to about 420° C. Operating pressures are typically in the range from about 40 to 350 bara, preferably 60 to 300 bara, more preferably 200 to 280 bara.

As used herein, "near supercritical conditions" means that the reactants and the solvent constitute a substantially single homogeneous phase; in practice, this can be achieved under conditions below the critical temperature for water. In one embodiment, the term "near supercritical conditions" means that the solvent is at a temperature which is not less than 100° C. below, preferably not less than 50° C. below, more preferably not less than 35° C. below and particularly not less than 20° C. below the critical temperature of water at 220.9 bara.

As used herein, "continuous flow reactor" means a reactor in which reactants are introduced and mixed and products withdrawn simultaneously in a continuous manner, as opposed to a batch-type reactor. For example, the reactor may be a tubular flow reactor (with either turbulent or laminar flow) although the various aspects of the invention defined herein are not limited to this particular type of continuous flow reactor. The residence time in the continuous flow reactor is defined as the reactor volume divided by the volumetric flowrate of the reactants at operating conditions.

As used herein, "carboxylic acid precursor" or "precursor" means an organic compound, preferably a hydrocarbon, capable of being oxidised to a specific carboxylic acid in a majority yield in the presence of selective oxidation conditions. An example of a pyridinecarboxylic acid precursor is methylpyridine, for instance, a nicotinic acid precursor is 3-methylpyridine. Correspondingly, methylpyrimidines can be used to produce pryimidine carboxylic acids.

As used herein, reference to the production of a carboxylic acid includes reference to the production of its anhydride. As will be evident to the skilled person, whether the processes of the present invention produce carboxylic acids or their anhydrides will depend on the conditions in the reaction and/or the conditions used to isolate or separate the products.

Preferably, in the process of the invention, substantially all, and in any event no less than 98% by wt, of heteroaromatic carboxylic acid produced in the reaction is maintained in solution during the reaction and does not begin to precipitate until the solution leaves the oxidation reaction zone and undergoes cooling.

The residence time for the reaction can be made compatible with the attainment of conversion of the precursor to the desired heteroaromatic carboxylic acid without significant production of degradation products. The residence time of the reaction medium within the reaction zone is generally no more than 10 minutes, usually of the order of 2 minutes or less, preferably 1 minute or less, and more preferably 30 seconds or less.

In a preferred embodiment, the selectivity for the target carboxylic acid is at least 90%, preferably at least 95%, and more preferably at least 98%, wherein the selectivity is the weight yield of the target acid divided by the combined weight yield of the target acid and the partially oxidised aldehyde impurity and other reaction products excluding degradation products, expressed as a percentage.

In preferred embodiment, the yield of the target carboxylic acid is preferably at least 50%, preferably at least 60%, preferably at least 70%, preferably at least 80%, and preferably at least 90% by weight of the weight of the precursor.

The reactor system suitable for performing the process of the present invention may be generally configured as described below. The following discussion relates to the preferred embodiment of a continuous flow reactor. However, as noted above, the invention is not limited to such a configuration and the following discussion is for the purposes of exemplification only.

There may be more than one reaction zone in series or in parallel. For instance, where multiple reaction zones in parallel are used, the reactants and solvent may form separate flow streams for passage through the reaction zones and, if desired, the product streams from such multiple reaction zones may be united to form a single product stream. Where more than one reaction zone is used, the conditions, such as temperature, may be the same or different in each reactor. Each reactor may be operated adiabatically or isothermally. Isothermal or a controlled temperature rise may be maintained by heat exchange to define a predetermined temperature profile as the reaction proceeds through the reactor.

In one embodiment of the invention, the heat of reaction is removed from the reaction by heat exchange with a heat-accepting fluid, according to conventional techniques known to those skilled in the art, for instance as described in WO-02/06201 the disclosure of which technique is incorporated herein by reference. Conveniently the heat-accepting fluid comprises water.

The oxidant in the process of the invention is preferably molecular oxygen, e.g. air or oxygen enriched air, but preferably comprises gas containing oxygen as the major constituent thereof, more preferably pure oxygen, or oxygen dissolved in liquid. The use of air is not favoured, although not excluded from the scope of the invention, since large compression costs would arise and offgas handling equipment would need to cope with large amounts of offgas owing to the high nitrogen content of air. Pure oxygen or oxygen enriched gas on the other hand permits use of a smaller compressor and smaller offgas treatment equipment. The use of dioxygen as the oxidant in the process of the invention is particularly advantageous since it is highly soluble in water under supercritical or near supercritical conditions. Thus, at a certain point, the oxygen/water system will become a single homogeneous phase.

Instead of molecular oxygen, the oxidant may comprise atomic oxygen derived from a compound, e.g. a liquid phase compound at room temperature, containing one or more oxygen atoms per molecule. One such compound for example is hydrogen peroxide, which acts as a source of oxygen by reaction or decomposition as described by Lin, Smith, et al (International Journal of Chemical Kinetics, Vol 23, 1991, p971).

The process of the invention is carried out in the presence of an oxidation catalyst. The catalyst may be soluble in the reaction medium comprising solvent and the heteroaromatic carboxylic acid precursors or, alternatively, a heterogeneous catalyst may be used. The catalyst, whether homogeneous or heterogeneous, typically comprises one or more heavy metal compounds, e.g. cobalt and/or manganese compounds, preferably manganese compound(s) alone, and may optionally include an oxidation promoter. For instance, the catalyst may take any of the forms that have been used in liquid phase oxidation reactions to produce aromatic carboxylic acids (such as terephthalic acid) in aliphatic carboxylic acid solvent, e.g. bromides, bromoalkanoates or alkanoates (usually $C_1$-$C_4$ alkanoates such as acetates) of cobalt and/or manganese. Compounds of other heavy metals, such as vanadium, chromium, iron, molybdenum, a lanthanide such as cerium, zirconium, hafnium, and/or nickel may be used instead of cobalt and/or manganese. Advantageously, the catalyst system will include manganese bromide ($MnBr_2$). The oxidation promoter where employed may be in the form of elemental bromine, ionic bromide (e.g. HBr, NaBr, KBr, $NH_4Br$) and/or organic bromide (e.g. bromobenzenes, benzyl-bromide, mono- and di-bromoacetic acid, bromoacetyl bromide, tetra-bromoethane, ethylene-di-bromide, etc.). Alternatively the oxidation promoter may comprise a ketone, such as methyl-ethyl ketone, or aldehyde, such as acetaldehyde.

Where the catalyst is in heterogeneous form, it may be suitably located within the reaction zone so as to secure contact between the continuously flowing reaction medium and the catalyst. In this event, the catalyst may be suitably supported and/or constrained within the reaction zone to secure such contact without unduly constricting the flow cross-section. For instance, the heterogeneous catalyst may be coated on or otherwise applied to, or embodied in, static elements (e.g. elements forming an openwork structure) positioned within the reaction zone so that the reaction medium flows over the same. Such static elements may additionally serve to enhance mixing of the reactants as they pass through the reaction zone. Alternatively the catalyst may be in the form of mobile pellets, particles, finely divided form, metal sponge form or the like with means being provided if necessary to confine the same to the reaction zone so that, in operation, the catalyst pellets etc become suspended or immersed in the reaction medium flowing through the reaction zone. The use of a heterogeneous catalyst in any of these ways confers the advantage of being able to confine the catalysis effect to a well-defined zone so that, once the reaction medium has traversed the zone, further oxidation takes place at a reduced rate or may be significantly suppressed.

The oxidation reaction is initiated by heating and pressurising the reactants followed by bringing the heated and pressurised reactants together in a reaction zone. This may be effected in a number of ways with one or both of the reactants being admixed with the aqueous solvent prior to or after attainment of supercritical or near supercritical conditions, such admixture being effected in such a way as to maintain the reactants isolated from one another until brought together in the reaction zone.

In the batch process of the present invention, water, precursor and catalyst solution are mixed in an autoclave before being heated to the reaction temperature and pressure. Oxidant may be optionally added to the mixture under reaction conditions, or it may be added prior to sealing and heating the batch reactor autoclave. After the desired reaction time, the reaction autoclave is cooled and the products discharged. Any suitable product recovery system such as extraction, concentration and recrystallisation may then be used to recover the heteroaromatic carboxylic acid product.

In the continuous process of the present invention, the reactor system is preferably configured such that the contact between the oxidant and at least part, and preferably substantially all, of a precursor is made at the same point in the reactor system as the contact between the catalyst and at least part, and preferably substantially all, of the oxidant.

In a first embodiment, the oxidant is mixed with the aqueous solvent after the latter has been heated and pressurised to secure the supercritical or near supercritical state, with suitable pressurisation and, if desired, heating, of the oxidant prior to mixing with the aqueous solvent. A precursor is subjected to pressurisation and, if desired, heating. In the case of a process using a homogeneous catalyst, the catalyst component is subjected to pressurisation and, if desired, heating. The precursor, the catalyst and the oxidant/solvent mixture are then contacted simultaneously. In the case of a process using a heterogeneous catalyst, a precursor is contacted with the oxidant/solvent mixture in the presence of the catalyst.

In a second embodiment of the invention, a precursor is mixed with the aqueous solvent after the latter has been heated and pressurised to secure the supercritical or near supercritical state, with suitable pressurisation and, if desired, heating, of the precursor prior to mixing with the aqueous solvent. In one arrangement, a homogenous catalyst component, after pressurisation and optional heating, is contacted with the aqueous solvent simultaneously with the contacting of a precursor with the aqueous solvent. In an alternative arrangement, a heterogeneous catalyst is used and confined to the reaction zone as described herein. The oxidant after pressurisation and, if desired, heating, is mixed with aqueous solvent after the latter has been heated and pressurised to secure the supercritical or near supercritical state. In the case of a process using a homogeneous catalyst, the oxidant/aqueous solvent mixture is then contacted with the mixture comprising a precursor, catalyst and aqueous solvent. In the case of a process using a heterogeneous catalyst, the oxidant/aqueous solvent mixture is contacted in the reaction zone, i.e. in the presence of the heterogeneous catalyst, with the mixture comprising a precursor and aqueous solvent.

Contact of the various streams may be effected by way of separate feeds to a device in which the feeds are united to form a single homogeneous fluid phase thus allowing the oxidant and precursor to react. The device in which the feeds are united may for instance have a Y, T, X or other configuration allowing separate feeds to be united in a single flow passage forming the continuous flow reactor, or in some circumstances multiple flow passages forming two or more continuous flow reactors. The flow passage or passages in which the feeds are united may comprise a section of tubular configuration with or without internal dynamic or static mixing elements.

In a preferred embodiment, in-line or static mixers are advantageously used to ensure rapid mixing and homogeneity, for example to promote dissolution of oxidant into the aqueous solvent and the formation of a single phase.

The oxidant feed and the precursor feed may be brought together at a single location or the contact may be effected in two or more stages so that at least part of one feed or of both feeds are introduced in a progressive manner, e.g. via multiple injection points, relative to the direction of flow through the reactor. For instance, one feed may be passed along a continuous flow passage into which the other feed is introduced at multiple points spaced apart lengthwise of the continuous flow passage so that the reaction is carried out progressively. The feed passed along the continuous flow passage may include the aqueous solvent as may the feed introduced at multiple positions.

Similarly, the addition of catalyst, particularly homogenous catalyst, may be effected in a progressive manner, e.g. via multiple injection points, relative to the direction of flow through the reactor.

In one embodiment, the oxidant is introduced to the reaction at two or more locations. Such locations are conveniently so positioned relative to the bulk flow of solvent and reactants through the oxidation zone that oxidant is introduced to the reaction at an initial location and at least one further location downstream of said initial location.

After traversing the continuous flow reactor, the reaction mixture comprises a solution of heteroaromatic carboxylic acid. The solution may also contain catalyst (if used), and relatively small quantities of by-products such as intermediates (e.g. aldehyde), decarboxylation products and degradation products and any unused reactants.

The invention will now be described further by way of example only with reference to the accompanying drawings in which:

FIGS. 1A and 1B are schematic flowsheets illustrating the basic arrangement described for the first embodiment above, wherein FIG. 1A illustrates use of a homogeneous catalyst, and FIG. 1B illustrates use of a heterogeneous catalyst.

FIGS. 2A-2D are schematic flowsheets illustrating the basic arrangement described for the second embodiment above, wherein FIGS. 2A and 2B illustrate use of a homogeneous catalyst and FIGS. 2C and 2D illustrate use of a heterogeneous catalyst. In FIGS. 2B and 2D, the oxidant is introduced in a progressive manner along the reaction zone at multiple injection points.

Figure 1A:
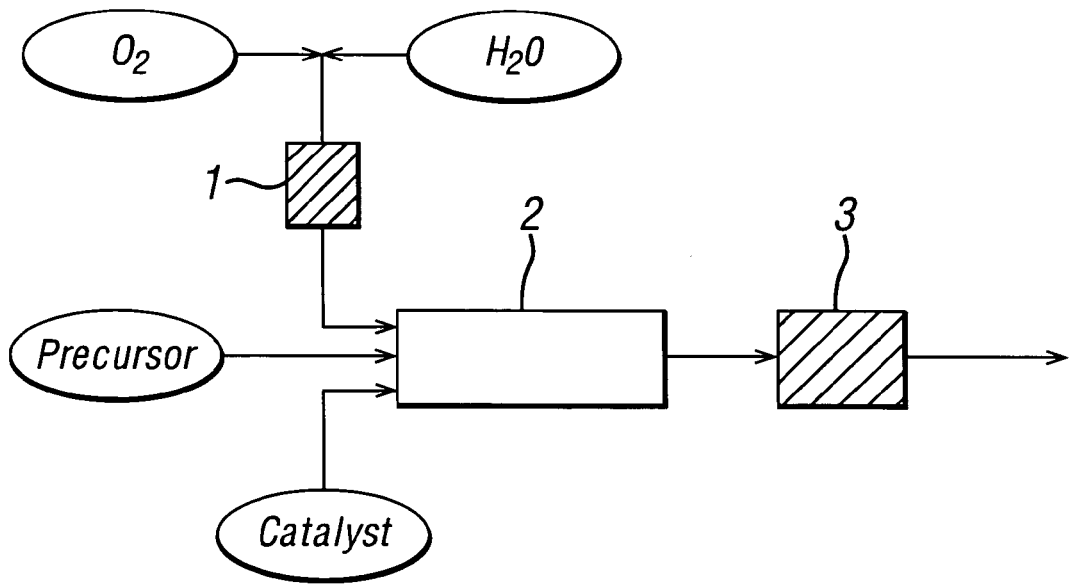

Referring to FIG. 1A, dioxygen, after pressurisation, is mixed with water after the water has been heated and the mixture pressurised and optionally further heated in preheater 1 to achieve the supercritical state. The precursor and catalyst are added, after pressurisation, to the $O_2$/water stream at the beginning of or immediately before the reactor 2 and the mixture passed through the reactor. Upon exiting the reactor, the stream is cooled and depressurised at the back-pressure regulator 3. The products are carried out in a stream of cooled water. In corresponding FIG. 1B, the catalyst is already present as a heterogeneous catalyst within the reactor.

Referring to FIGS. 2A and 2B, the precursor and catalyst, after pressurisation are added to water after the water has been pressurised and optionally heated, and optionally further heated in preheater 1A to achieve the supercritical state. The dioxygen gas, after pressurisation is mixed with water at a supercritical state and optionally further heated in preheater 1. In FIG. 2A, the two streams are mixed at the beginning of or immediately before the reactor 2 and the mixture passed through the reactor. In FIG. 2B, the $O_2$/water stream is added to the reactor in a progressive manner at multiple injection points. Upon exiting the reactor, the stream is cooled and depressurised at the back pressure regulator 3. The products are carried out in a stream of cooled water. In corresponding FIGS. 2C and 2D, the catalyst is already present as a heterogeneous catalyst within the reactor.

Figure 3:
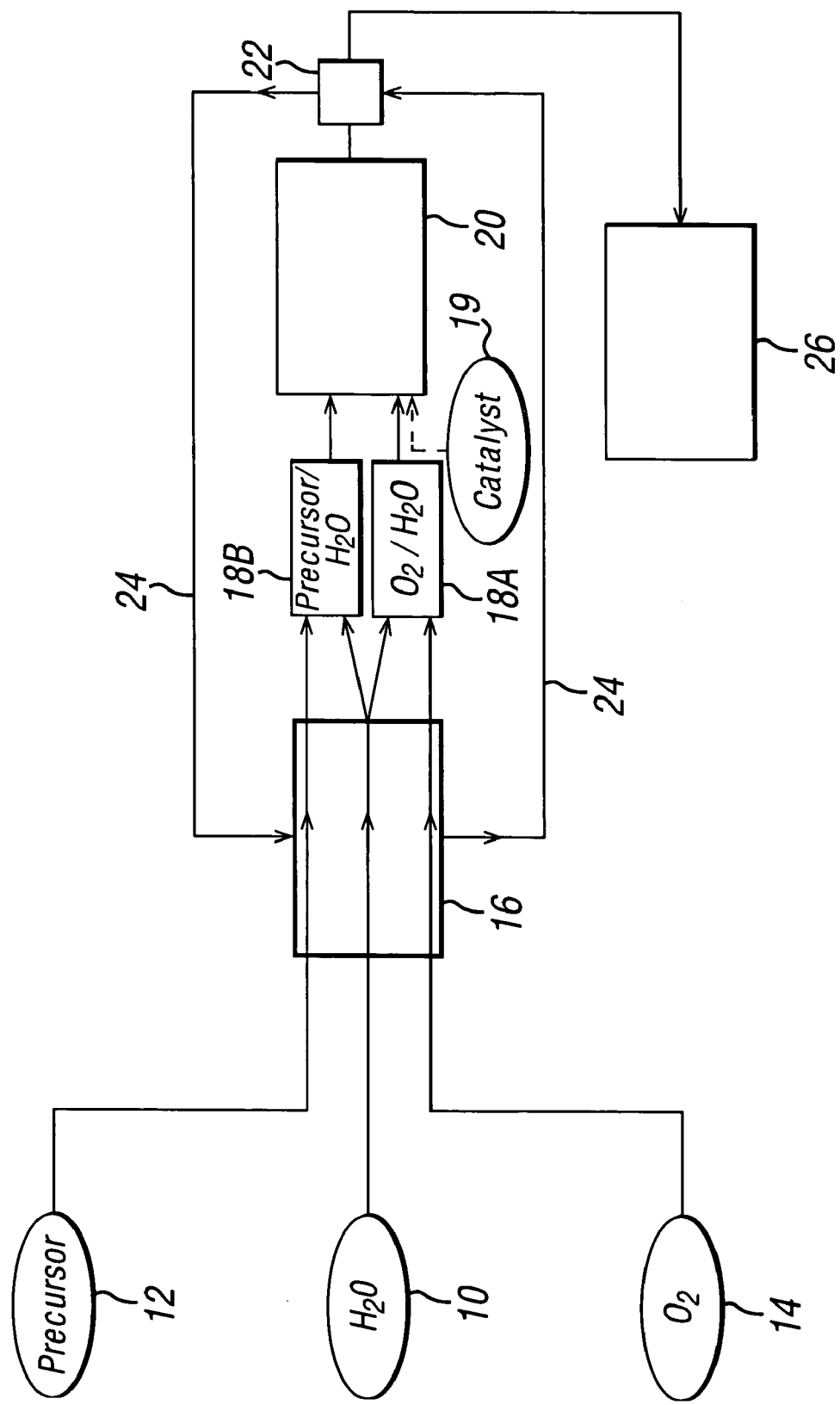
FIG. 3 is a schematic flowsheet illustrating in more detail an arrangement wherein the precursor is added to a premixed stream of oxygen and water (i.e. an arrangement according to the process illustrated in FIG. 1A or 1B).
Figure 4A:
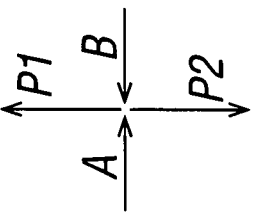
FIGS. 4A, 4B, 4C, 4D and 5 illustrate various premixer configurations that may be employed to effect mixing of at least one of the reactants with the aqueous solvent.
Figure 4B:
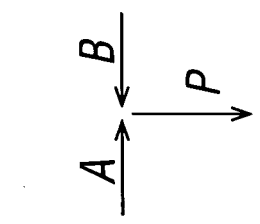
Figure 4C:
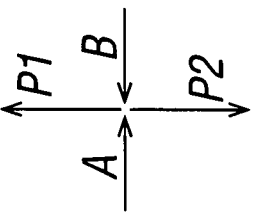
Figure 4D:
Figure 5:
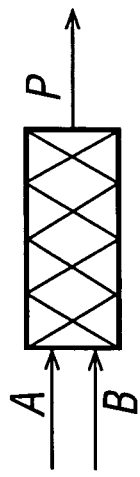

Referring to FIG. 3, feedstock components comprising water, precursor and dioxygen gas are pressurised to operating pressure and continuously supplied from respective sources 10, 12 and 14 through a preheater 16 where the components are heated to a temperature of 300° to 480° C., more preferably 330° to 450° C., typically from about a lower limit of about 340° to 370° C. to an upper limit of about 370° to about 420° C., the pressure and temperature being selected in order to secure supercritical or near supercritical conditions. Part of the heat used to preheat the feedstock components may be derived from the exotherm produced in the course of the subsequent reaction between the precursor and the oxidant. Heat from other sources may be, for example, in the form of high pressure steam and/or heating may be effected by direct fired heating of the water stream. The heat of reaction may be recovered in any suitable manner, e.g. by means of heat exchange between the fluid following reaction and a suitable heat-accepting fluid such as water. For instance, the heat-accepting fluid may be arranged to flow in heat exchange relation, countercurrently and/or co-currently, with the reactants and solvent passing through the reaction zone. The passage or passages along which the heat-accepting fluid flows in traversing the reaction zone may be external to the reaction zone and/or may extend internally through the reaction zone. Such internally extending flow passage(s) may for instance extend generally parallel with and/or transversely of the general direction of flow of the reactant/solvent through the reaction zone. For example, the heat-accepting fluid may traverse the reaction zone by passage through one or more coiled tubes located within the interior of the reactor. The enthalpy of reaction can be used to recover power via a suitable power recovery system such as a turbine; for instance the heat-accepting fluid, e.g. water, can be used to raise high pressure saturated steam at for example temperature and pressure of the order of 300° C./100 bara which, in turn, can be superheated by external heat and fed to a high efficiency condensing steam turbine to recover power. In this way, the reactor can be maintained at an optimum temperature and effective energy efficiency can be achieved. In an alternative approach, the reactor may be operated under adiabatic conditions and a suitably high rate of water flow through the reaction zone may be employed in order to constrain the temperature rise across the reactor in operation. If desired, a combination of both approaches may be used, i.e. recovery of the enthalpy of reaction via a heat-accepting fluid coupled with a suitable water flow rate through the reaction zone.

Following heating of the feedstock components, oxygen is mixed with water which, as a result of preheating and pressurisation, will be under supercritical or near supercritical conditions and hence capable of solubilizing the feedstock. In the embodiment illustrated in FIG. 3, oxygen and water are mixed in premixer 18A. Precursor is also mixed with water in premixer 18B. Of course, a precursor could also be separately premixed with water prior to entry into the preheater 16.

The premixer (or premixers where premixing of each reactant and water is undertaken) may take various forms such as Y, L or T piece, double T configurations or a static mixer, as illustrated in FIGS. 4A, 4B, 4C, 4D and 5 respectively. In FIGS. 4A to 4D and 5, reference A depicts the preheated water supply to the premixer, B depicts the reactant (precursor or oxygen) and P depicts the resulting mixed stream. In the double T configuration of FIG. 4D, two mixed streams are produced P1 and P2. These may either be passed through separate continuous flow reactors or be combined into a single stream and then passed through a single continuous flow reactor. An X piece configuration may also be used, as known to those skilled in the art.

It will be appreciated that instead of premixing one or both reactants with water prior to introduction into the reaction zone, the reactants and water may be introduced separately into the reaction zone and mixed within the reaction zone with the aid of some form of mixing arrangement (e.g. a static mixer) whereby substantially all mixing of the components occurs within the reaction zone.

Where a homogeneous catalyst is to be employed in the reaction, the catalyst is added as a solution from source 19 to the premixed oxygen/water stream at the same time as the precursor is added to the premixed oxygen/water stream either immediately prior to entering the reactor or at the beginning of the reactor (i.e. as shown in FIG. 1A).

Figure 1B:
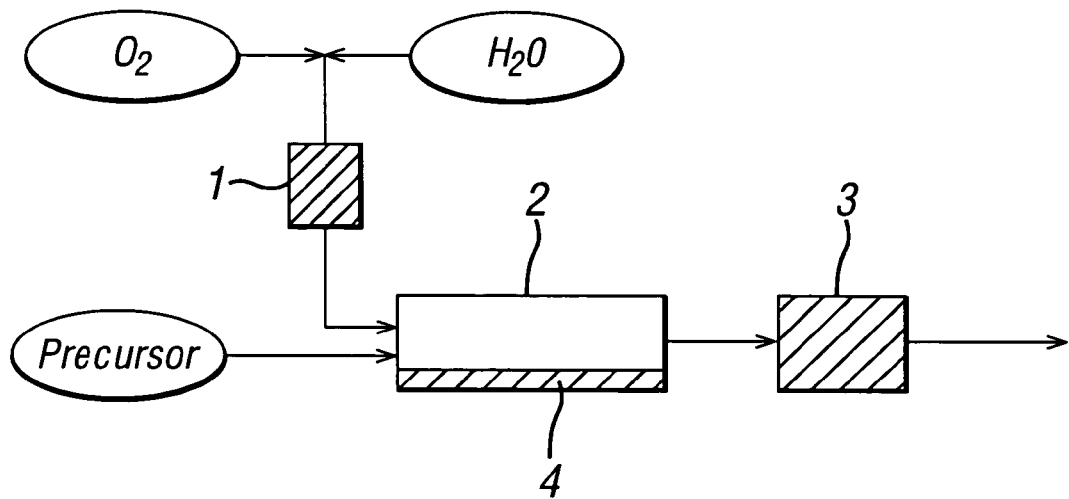

Following preheating and premixing, the feedstock components are combined in a reaction zone 20 to form a single homogeneous fluid phase in which the reactants are brought together. The reaction zone 20 may consist of a simple mixer arrangement in the form of a tubular plug flow reactor, e.g. a pipe of a length which, in conjunction with the flow rate of the combined reactants, provides a suitable reaction time so as to secure conversion of the precursor to the carboxylic acid with high conversion efficiency and low intermediate aldehyde content.

Where the reaction is carried out in the presence of a heterogeneous catalyst system (i.e. as shown in FIG. 1B), the catalyst system may be distributed lengthwise with respect to the flow direction and may be co-extensive with the reaction zone so that, once the supercritical or near supercritical fluid passes beyond the section of the pipe occupied by the catalyst system, the rate of reaction falls significantly to suppress the production of degradation products.

Figure 6:
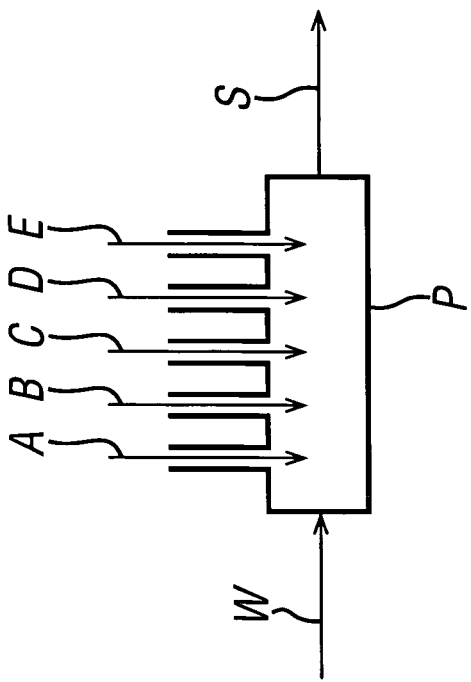
FIG. 6 is a schematic view illustrating multiple stage injection of oxidant.

The reactants may be combined in "one shot" upstream of the reactor 20. Alternatively, they may be combined in a progressive manner by injecting one reactant into a stream containing the other reactant at multiple points along the length of the reactor. One way of implementing a multiple injection arrangement is shown in the continuous flow reactor of FIG. 6 in which the reactor is constituted by a pipe P. In an embodiment wherein a premixed oxygen/water stream is added to a premixed precursor/water stream (as shown in FIG. 2D) a premixed precursor/supercritical or near supercritical water stream W is supplied to the upstream end of pipe P. For a process in which homogeneous catalysts are used, water stream W would also contain the catalyst; in a process using heterogeneous catalysts, the catalysts would be present inside pipe P. The stream passes through the reactor pipe P and at a series of locations spaced at intervals along the length of the pipe P, preheated and compressed oxygen dissolved in supercritical or near supercritical water is supplied via injection passages A to E to produce a product stream S comprising the desired heteroaromatic carboxylic acid in supercritical or near supercritical aqueous solution. In this manner, the oxygen necessary to effect complete oxidation of precursor to the carboxylic acid is injected progressively with the aim of controlling oxidation and minimising side reactions and possible burning of precursor, the carboxylic acid product or the carboxylic acid intermediates.

Referring now back to FIG. 3, following the reaction to the desired degree, the supercritical or near supercritical fluid is passed through a heat exchanger 22 through which heat exchange fluid is circulated via closed loop 24 so that heat can be recovered for use in the preheater 16. The cooled solution is then supplied to a product recovery section 26 in which the carboxylic acid is recovered from the solution. Any suitable method of product recovery known to those skilled in the art may be used.

EXAMPLES

Figure 7:
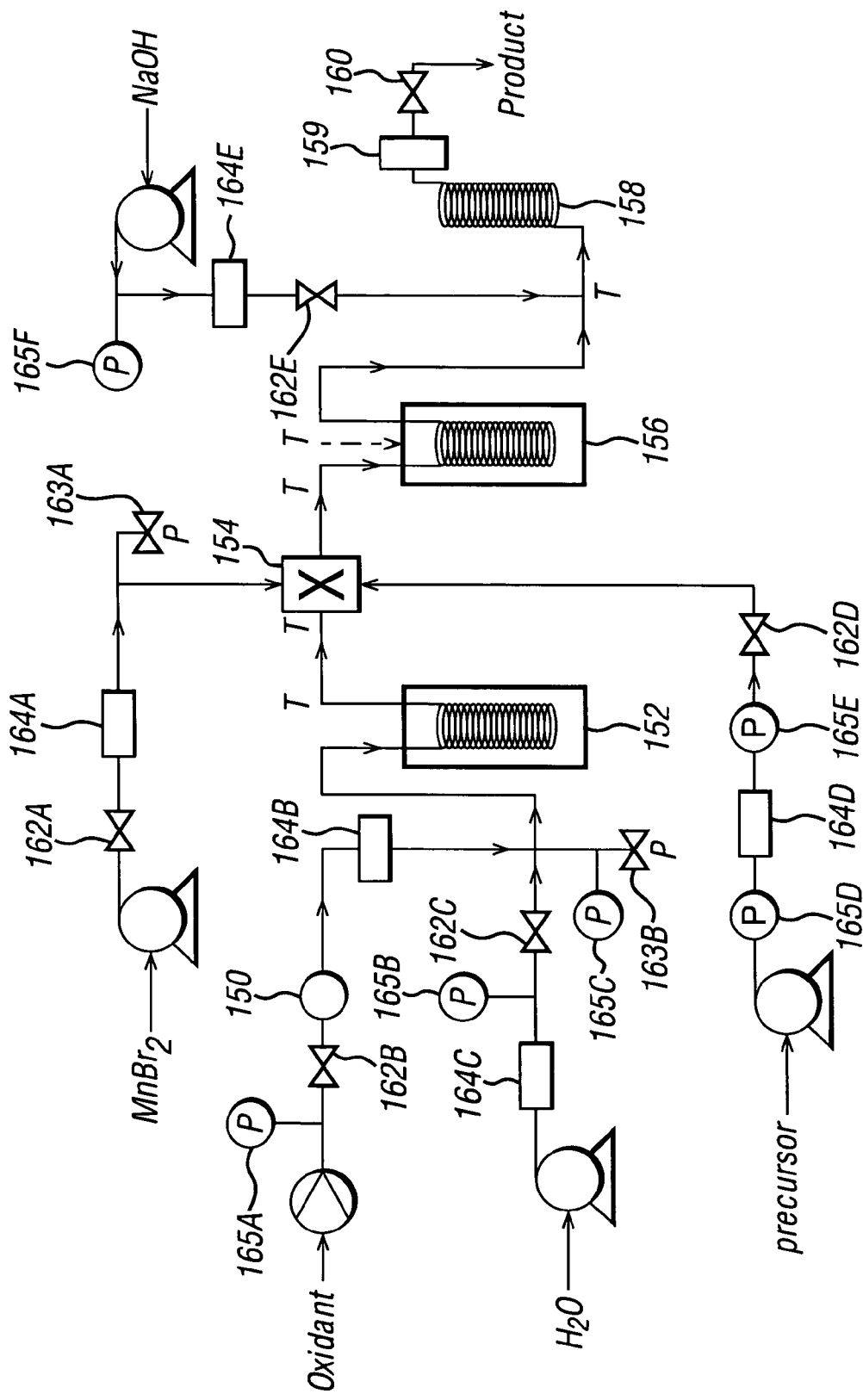
FIG. 7 is described hereafter in relation to the Examples.

Experimental work was carried out on a laboratory scale by the continuous oxidation of precursor in supercritical water with an $MnBr_2$ catalyst. The exotherm was minimised by using relatively dilute solutions (<5% organic w/w). The basic configuration of the system is as set out in FIG. 1A. A more detailed illustration of the system used in these laboratory scale experiments is shown in FIG. 7.

Hydrogen peroxide (100 volume) was diluted to an appropriate concentration such as a 2% solution, fed to a pump, cooled to 5° C. or less. The hydrogen peroxide was then heated in preheater 152 consisting of a 5 m coil of ¼ inch O.D. stainless steel tubing cast into an aluminium block. Adequate mixing of oxidant and water was achieved by using a relatively long coil in the preheater 152. The oxidant/water fluid was then passed through the cross piece 154, where it was contacted with the precursor and solution of $MnBr_2$ catalyst, fed in from their own pumps.

Other components are labelled in FIG. 7 as follows: 162 A-E: valves; 163 A-B: pressure release valves; 164 A-E: non-return valves; 165 A-F: pressure transducers; T: thermocouple (the aluminium heater block of preheater 152 contains a thermocouple, not shown). The preheater was obtained from NWA GmbH; the pumps were Gilson 302, 305, 306 and 303; the back pressure regulator obtained from Tescom (model 26-1722-24-090).

Maximum corrosion occurs in the region of the crosspiece 154 where oxidant, precursor and the catalyst solution meet, particularly at the incoming unheated catalyst feed pipe where a high temperature gradient coincides with bromide ions. Hastelloy C276 (or titanium) was used for the final section of the catalyst feed-pipe and downstream of the reactor, before the mixer section for addition of NaOH solution, if used, where a temperature gradient of approximately 100° C. occurs over a length of approximately 5 cm, and 316L stainless steel for the other components. All pipe work liable to corrosive failure is protected inside polycarbonate shielding.

Before each run, the apparatus is hydrostatically pressure tested when cold, and is then heated with a flow of pure 18 Mohm water (5-10 ml min). Once the operating temperature was reached, the hydrogen peroxide feed and the pumps for precursor and $MnBr_2$ were started. Typically, an experiment was run for 4 to 5 hours. The products were usually collected for sequential periods of 15 or 30 minutes and analysed. Purity was verified principally by HPLC. The yield of solid product was calculated as the molar concentration of the different products in the solution divided by the molar concentration of the feedstock fed to the reactor.

Example 1

Using 100 volume of hydrogen peroxide, a dilute stock solution was prepared using 56 ml of peroxide and 760 ml of nanopure water (18.3 megohm resistance). A dilute catalyst stock solution was prepared by dissolving manganese bromide in nanopure water to a concentration of 5000 ppm w/w of Br. 3-Methylpyridine was held separately undiluted. A stock solution of sodium hydroxide (0.5M) was prepared to feed downstream of the reactor, but before the back-pressure regulator.

De-ionised water alone was pumped through the preheater, mixing-piece, reactor, caustic mixer, cooler and back-pressure regulator at a rate to control the final residence time through the reactor to 10 seconds. The residence time was defined as the volume of the tubular reactor, pipework and fittings between the mixing pieces; the first to mix the reactants to initiate the reaction and the second to quench the reaction with the addition of sodium hydroxide, divided by the volumetric flowrate. The volumetric flowrate was based on the physical properties of water at the mixing conditions, as published in International Steam Tables and by U.S. National Institute of Standards and Technology.

The back-pressure regulator was set to control the reactor pressure at 220 bar. The heaters were set to control the mixing piece at 380° C. and the reactor at 374° C.

Each of the reactants was pumped separately to the mixing piece. Methylpyridine was fed at a concentration of 0.50% w/w to the reactor, oxygen was fed at slightly greater than the stoichiometric rates required for the oxidation of 3-methylpyridine to nicotinic acid and catalyst solution was fed to the mixing piece to generate a concentration of 1640 ppm Br in the reactor.

After reaching stable set-point conditions samples were collected over a 15 minute interval and subsequently analysed. This experiment was run for 1.5 hours. The results show good selectivity for nicotinic acid (around 95%) at a conversion of about 30%. Some 3-pyridine carboxaldehyde was detected with a yield of 1-2%. Unreacted precursor is stable in the reaction medium and is recovered at the end of the reaction.

The invention claimed is:

1. A process for the production of a heteroaromatic carboxylic acid wherein the heteroaromatic is a pyridine ring or a pyrimidine ring, the process comprising contacting, in the presence of an oxidation catalyst comprising one or more heavy metal compounds, an alkyl-substituted heteroaromatic compound with an oxidant to form said heteroaromatic carboxylic acid, such contact being effected with said alkyl-substituted heteroaromatic compound and the oxidant in an aqueous solvent comprising water under supercritical conditions or near supercritical conditions close to the supercritical point, wherein said one or more heavy metal compounds are selected from the group consisting of cobalt, manganese, vanadium, chromium, iron, molybdenum, cerium, zirconium, hafnium and nickel.

2. A process according to claim 1 wherein said contact is effected within a continuous flow reactor.

3. A process according to claim 2 wherein the contacting of the alkyl-substituted heteroaromatic compound occurs in a reaction zone wherein the residence time is less than 2 minutes.

4. A process according to claim 3 wherein no less than 98% by weight of the heteroaromatic carboxylic acid produced is maintained in solution during the reaction.

5. A process according to claim 1 wherein the heteroaromatic carboxylic acid has a pyridine ring.

6. A process according to claim 1 wherein the heteroaromatic carboxylic acid is nicotinic acid.

7. A process according to claim 1 wherein the alkyl-substituted heteroaromatic compound is an alkylpyridine.

8. A process according to claim 1 wherein the alkyl-substituted heteroaromatic compound is 3-methylpyridine.

* * * * *